(12) United States Patent
Colpaert et al.

(10) Patent No.: US 8,609,694 B2
(45) Date of Patent: Dec. 17, 2013

(54) USE OF PYRIDIN-2-YL-METHYLAMINE DERIVATIVES FOR THE PRODUCTION OF A MEDICAMENT FOR THE TREATMENT OF CHRONIC PAIN SYMPTOMS OF NEUROPATHOLOGICAL OR PSYCHOGENIC ORIGIN

(75) Inventors: Francis Colpaert, Puylaurens (FR); Bernard Vacher, Castres (FR)

(73) Assignee: Pierre Fabre Medicament (FR)

( * ) Notice: Subject to any disclaimer, the term of this patent is extended or adjusted under 35 U.S.C. 154(b) by 1557 days.

(21) Appl. No.: 10/549,076

(22) PCT Filed: Mar. 15, 2004

(86) PCT No.: PCT/FR2004/000630
§ 371 (c)(1),
(2), (4) Date: Jun. 27, 2006

(87) PCT Pub. No.: WO2004/083171
PCT Pub. Date: Sep. 30, 2004

(65) Prior Publication Data
US 2006/0241141 A1    Oct. 26, 2006

(30) Foreign Application Priority Data
Mar. 13, 2003  (FR) ..................... 03 03099

(51) Int. Cl.
*A61K 31/445* (2006.01)
(52) U.S. Cl.
USPC ............................ 514/318; 546/194; 546/226
(58) Field of Classification Search
USPC .................... 514/318; 546/194, 226
See application file for complete search history.

(56) References Cited

U.S. PATENT DOCUMENTS 6,020,345 A * 2/2000 Vacher et al. ................ 514/318
6,448,268 B1 * 9/2002 Vacher et al. ................ 514/318

FOREIGN PATENT DOCUMENTS

| WO | WO-98/22459 A | 5/1998 |
| WO | WO-00/21953 A | 4/2000 |
| WO | WO-03/106449 A | 12/2003 |

OTHER PUBLICATIONS

Vacher et al. "Novel derivatives of 2-pyridinemethylamine . . . " J. Med. Chem. v.42, p. 1648-1660 (1999).*
Bardin et al. "Profound nonopioid . . . " Pharmacology v.67, p. 182-194 (2003).*
Colpaert, et al. "Large-amplitude 5-HT1A receptor activation: a new mechanism of profound, central analgesia", Neuropharmacology, vol. 42, pp. 945-958, 2002 Elsevier Science Ltd.
Deseure, et al., "The 5-HT1A receptor agonist F 13640 attenuates mechanical allodynia in a rat model of trigeminal neuropathic pain", European Journal of Pharmacology, No. 456, pp. 51-57, 2002 Elsevier Science B.V.
Bruins, et al., "Tolerance and inverse tolerance to the hyperalgesic and analgesic actions, respectively, of the novel analgesic, F 13640", European Journal of Pharmacology, vol. 466, pp. 271-279, 2003 Elsevier Science B.V.

(Continued)

*Primary Examiner* — Celia Chang
(74) *Attorney, Agent, or Firm* — Lerner, David, Littenberg, Krumholz & Mentlik, LLP (57) ABSTRACT

This invention relates to a treatment of chronic pain symptoms, especially of neuropathological or psychogenic origin, with pyridin-2-yl methylamine derivatives or pharmaceutically acceptable additive salts thereof.

7 Claims, 4 Drawing Sheets

(56) References Cited

OTHER PUBLICATIONS

Hoa, et al., "Treatment of a chronic allodynia-like response in spinally injured rats: effects of systemically administered excitatory amino acid receptor antagonists", Pin, vol. 66, pp. 279-285, 1996 International Association for the Study of Pain.

Vos, et al., "Behavioral Evidence of Trigeminal Neuropathic Pain Following Chronic Constriction Injury to the Rat's Infraorbital Nerve", The Journal of Neurosciences, vol. 14, No. 5, pp. 2708-2723, May 1994.

Colpaert et al., European Journal of Pharmacology, 497; 29-33 (2004).

* cited by examiner

USE OF PYRIDIN-2-YL-METHYLAMINE DERIVATIVES FOR THE PRODUCTION OF A MEDICAMENT FOR THE TREATMENT OF CHRONIC PAIN SYMPTOMS OF NEUROPATHOLOGICAL OR PSYCHOGENIC ORIGIN

The present invention relates to the use of pyridine-2-yl-methylamine derivatives for the preparation of a drug intended for the curative treatment of neuropathic and psychogenic chronic pain symptoms.

In international patent application WO 98/22459, the Applicant described compounds of general formula (I):

(I)

Compounds of general formula (I) are characterized by their affinity and selectivity for 5-HT$_{1A}$ receptor subtypes, as well as by their capacity to provoke a specific element of serotonin syndrome (i.e., lower lip retraction) in the rat after oral administration. For this reason, compounds of formula (I) are claimed as potentially useful drugs for the treatment of depression and pain.

One aim of the present invention is to improve existing analgesic techniques and treatments by means of compounds of general formula (I). The claimed improvements open new therapeutic prospects for the preventive and/or curative treatment of chronic pain symptoms for which there is not, currently, a satisfactory therapeutic solution.

In general, three types of chronic pain are classified according to the mechanism implicated, namely, pain that results from excess nociceptive stimulation, neuropathic pain (or neurogenic or from deafferentation), and psychogenic pain. However, some pain possesses characteristics common to several types of pain.

The expression "chronic pain" used within the scope of this patent application encompasses pain syndromes whose development lasts beyond three months, but whose intensity may vary over time.

Within the scope of the present invention, pain is defined as an abnormal sensory and emotional experience which ranges from unpleasant to painful, and which is perceived and integrated at the highest level of the cerebral cortex where its emotional and affective tone are imparted.

Within the scope of the present invention, the expression "neuropathic pain" targets all pain that originates from one or more lesions and/or dysfunctions of the central or peripheral nervous system.

Within the scope of the present invention, the expression "psychogenic pain" indicates, in general, pain which does not have an apparent pathological cause. This is pain without a true anatomical foundation, which is to say, without an objective lesion, and it is primarily psychological or psychical. Thus, it may be an issue known as "phantom" pain, i.e., an initial organic pain that persists after the causal lesion (pain memory) disappears, or a true hallucination of pain (pain felt in an amputated body part), or an organic pain for which no lesion is discovered. This type of pain may be perceived in various regions of the body and with widely diverse manifestations and intensities.

Thus, the present invention targets the treatment of symptoms of "erratic" pain, i.e., pain that frequently changes location.

The present invention also targets the treatment of other pain such as: "heavy" pain, i.e., pain accompanied by a feeling of heaviness; "stabbing" pain, i.e., pain comparable with that which would be caused by a stab; "dull" pain, i.e., light but continuous pain; "tensive" pain, i.e., pain accompanied by a feeling by distension; and "terebrant" pain, i.e., intense, deep pain that the patient perceives as if it were produced by a pointed object inserted into the patient's body.

By "analgesic drugs" is meant drugs which relieve or suppress pain without the loss of sensation or consciousness.

In summary, the present invention targets the treatment of symptoms not which correspond to pain that results from excess nociceptive stimulation, but for which neuropathic and psychogenic pain no longer has any physiological role but which has become truly pathological, in the form of a signal, for example.

Thus, the present invention relates to the preparation of drugs intended for the preventive and/or curative treatment of chronic pain symptoms of neuropathic or psychogenic origin.

The drugs used in clinical practice to treat chronic pain are derived from three distinct pharmacological families whose best-known members include: morphine, aspirin, and acetaminophen. Morphine acts on the central nervous system and remains the central analgesic of reference. Aspirin acts on the peripheral nervous system, directly on the cause of pain. Acetaminophen acts similarly to aspirin but may also involve a central action. The drugs that belong to these various families are effective against pain that results from excess nociceptive stimulation, but little or not at all for the other types of pain (i.e., neuropathic pain and psychogenic pain). So to relieve certain neuropathic pain of low or moderate intensity there is, in practice, recourse to antidepressant agents, primarily to those members of the class of tricyclics (amitriptyline and imipramine, for example) Other auxiliary drugs such as anxiolytics, anticonvulsants (gabapentine and carbamazepine, for example), sodium channel blockers (lidocaine, mexiletine), or glucocorticoids are also prescribed in association with both morphine and non-morphine based analgesics. In addition to the relatively limited effectiveness of current drugs, their chronic use is accompanied, moreover, by undesirable side effects. Examples of side effects include: tolerance and dependence problems related to the use of the major morphines (morphine and pethidine, for example); digestive toxicity (aspirin and salicylated derivatives, for example); hypotension, sedation, and weight gain (tricyclic antidepressants), etc.

In comparison to the drugs used in clinical practice, a number of compounds which use different mechanisms of action are at various stages of study as analgesics. These include, for example, 5-HT$_{1A}$ agonists (WO 98/22459, for example), serotonin reuptake inhibitors (E-5296); serotonin and adrenalin reuptake inhibitors (venlafaxine); cholinergic agonists (levetiracetam); NMDA antagonists (memantine, CNS-5161); glutamate antagonists (topiramate); nicotinic receptor modulators (ABT-594); CCK antagonists (colykade, devacade); capsaicin derivatives (DA-5018, BL-1832); cannabinoids derivatives (CT-3); nociceptin antagonists (JTC-801), etc. These compounds are, for the most part, claimed as agents for the symptomatic treatment of neuropathic pain.

Thus, it emerges overall that:

current chronic pain treatments are essentially founded on treating the cause (anti-inflammatories, for example) and, as a result, have little or no effect on neuropathic and psychogenic pain;

therapeutic approaches which address the problems of neuropathic and psychogenic pain (antidepressants and morphine, for example) relieve symptoms at best but do not have any curative action; their use, moreover, is limited by their side effects;

new approaches may benefit from a wider range of action than with conventional agents with respect to symptomatic treatment of chronic pain, but there are no claims of an effect which in any way resembles a curative effect.

The present application claims an improvement in the treatments and techniques for chronic pain syndromes of neuropathic or psychogenic origin for which therapeutic need is significant. The advantages of the technical improvements which are the subject of the application are:

that the analgesia obtained by means of a $5\text{-}HT1_A$ agonist of formula (I) extends beyond the classical symptomatic treatment for chronic pain of neuropathic or psychogenic origin;

that the analgesia obtained by means of a $5\text{-}HT1_A$ agonist of formula (I) over time decreased, even permanently, the pain intensity level perceived in the context of neuropathic and psychogenic pain;

that the activity of compounds of general formula (I) may be similar in curative action for chronic pain of neuropathic or psychogenic origin; to date, no action of this type has been reported for any another agent that possesses analgesic properties including, among others, $5\text{-}HT1_A$ agonists.

The present invention will now be further described by way of illustration with reference to the accompanying examples and figures in which.

With respect to a symptomatic pain syndrome treatment plan, some compounds of general formula (I) possess a powerful analgesic activity in representative animal models of neuropathic pain. In fact, it has already been established that their analgesic activity generally surpasses the activity produced by reference analgesics. However, during the study of the analgesic activity of compounds of formula (I) in subchronic and chronic administration, the inventors demonstrated unexpected properties of considerable scope in terms of therapeutic application for the treatment of chronic pain.

Figure 1:
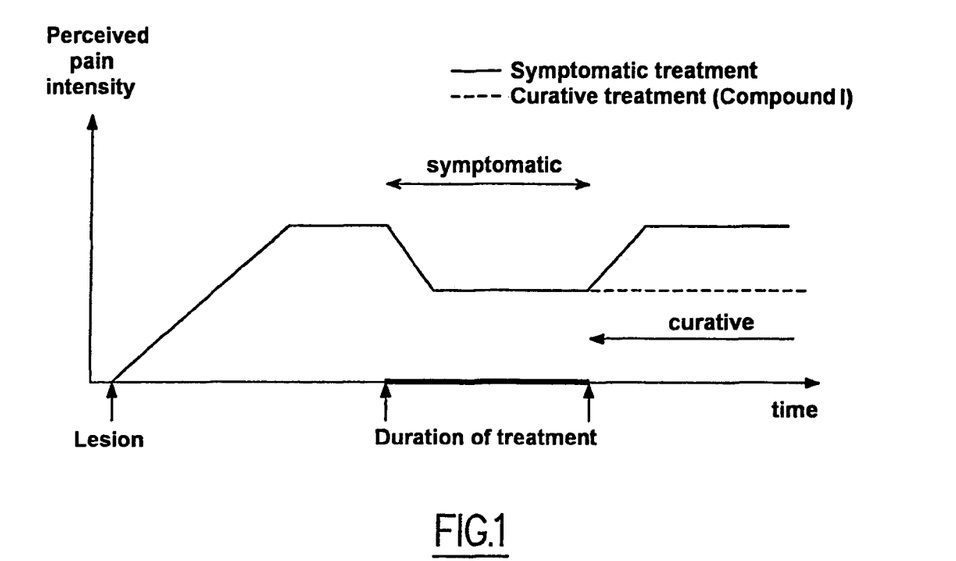
FIG. 1 shows the analgesic activity profile of an active compound when the active analgesic agent is administered during the chronic pain phase.
Figure 2:
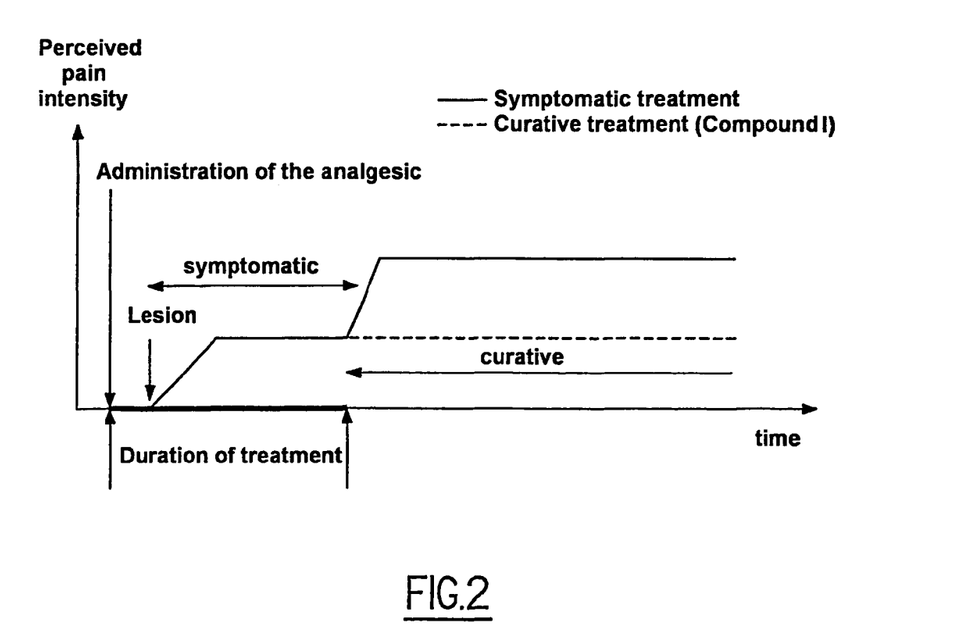
FIG. 2 shows the analgesic activity profile of an active compound, when chronic treatment in the animal is initiated before the induction of pain.

Indeed, regardless of the mode of action, all analgesic agents present typical similar in vivo activity profiles, which can be described as symptomatic as shown in FIGS. 1 and 2 in the appendix. However, in addition to the classical symptomatic analgesia phase, compounds of formula (I) produce a curative phase of analgesia not previously reported for any analgesic agent or regime. The nature of this specific analgesia phase is detailed below.

In practice, two temporally different treatment plans may be distinguished:

a) the active analgesic agent is administered during the chronic pain phase;

b) administration of the active analgesic agent precedes the appearance of chronic pain.

a) The Active Analgesic Agent is Administered During the Chronic Pain Phase

In animals that have developed chronic pain (hyperalgia or allodynia) of maximum amplitude intensity, such as presented in FIG. 1 in the appendix, chronic administration of an active analgesic agent results in a significant, and in theory dose dependant, decrease in the intensity of perceived symptoms (i.e., symptomatic analgesia). The intensity of perceived symptoms of pain may be objectified by measuring various behavioral, physiological, conscious, and unconscious parameters. The analgesic effect is maintained as long as circulating levels of the analgesic agent are sufficient to exert analgesic influence. When treatment is interrupted, the intensity of perceived pain increases and tends to settle at a level near its initial level (i.e., the pre-treatment pain threshold). The intensity of perceived pain may also increase during the treatment phase if a phenomenon of tolerance to the analgesic agent develops (treatment with major morphines, for example).

In the case of the chronic administration of certain compounds of general formula (I), the classical dose dependant decrease of the intensity of perceived symptoms (i.e., classical symptomatic analgesia) is also observed during the treatment phase. However, contrary to other analgesics, the intensity of perceived pain does not tend to find its initial level when the treatment is interrupted, such as appears in FIG. 1 in the appendix. Thus, quite surprisingly, not only does analgesia persist in spite of the end of treatment but it is maintained at a stable level at the same amplitude as that reached at the treatment's end. The phenomenon observed is all the more interesting because compound (I) is not no longer present in the animals' bodies during the subsequent analgesia phase at the treatment's end, and because it has no effect on the causes of chronic pain (lesion and inflammation, for example). Under these conditions, the actions of compound (I) perhaps qualify as curative. The mechanisms implied in the specific mode of action of compounds of formula (I), downstream from the activation of $5\text{-}HT1_A$ receptors, remain unknown.

b) Administration of the Active Analgesic Agent Precedes the Appearance of Chronic Pain

The classical analgesic activity profile of an active compound, when chronic treatment in the animal is initiated before the induction of pain (such as appears in FIG. 2 in the appendix), shows that the perceived intensity of pain following the lesion reaches a amplitude threshold that is lower than the threshold reached in the absence of treatment (i.e., the classical symptomatic analgesic effect). This phase of symptomatic analgesia disappears systematically when treatment is interrupted (such as appears in FIG. 2 in the appendix).

In the case of the chronic administration of certain compounds of general formula (I), when treatment is initiated before the induction of pain, the phase of symptomatic analgesia characteristic of active analgesics is also observed. However, as in case a) the analgesia produced by compounds of formula (I) persists and is maintained at a stable level in spite of the treatment's end (such as appears in FIG. 2 in the appendix). During this specific phase of analgesia, compound (I) is no longer present in the animals' bodies and has no effect on the cause of chronic pain. Thus, a treatment by means of a compound (I) which precedes the appearance of chronic pain tends to prevent or strongly attenuate later pain development. This specific aspect of the activity of compounds of formula (I) is potentially advantageous for the preventive treatment of postoperative pain. Such a treatment may also be useful for certain nervous system attacks in which a more or less significant delay separates the lesion from the appearance of pain (rachidian lesions and phantom pain, for example).

The unique and unexpected analgesic activity development profile of compounds of formula (I), in particular by their curative action and regardless of the treatment plan (i.e., before or after pain develops), represents a substantial improvement in the current state of the art.

Thus, compounds of the invention make it possible, potentially, to respond to a therapeutic need in the field of treatment of chronic pain of neuropathic and/or psychogenic origin in which the drugs available prove to have little or no effectiveness or prove of limited utility due to their side effects.

Compounds (I) are represented, in base form, by general formula (I):

(I)

in which:
  u represents a hydrogen atom or a methyl radical under the condition that when u is a methyl radical then v and w represent hydrogen atoms;
  v represents a hydrogen atom, a chlorine atom, or a methyl radical under the condition that when v is a methyl radical then u and w represent hydrogen atoms;
  w represents a hydrogen atom, a fluorine atom, or a methyl radical under the condition that when w is a methyl radical then u and v represent hydrogen atoms;
  x represents an atom of hydrogen or fluorine;
  y represents a chlorine atom or a methyl radical;
  z represents an atom of hydrogen, fluorine, or chlorine, or a methyl radical;
  A represents:
    an atom of hydrogen, fluorine, or chlorine;
    a C1-C5 alkyl radical, i.e., straight or branched saturated aliphatic hydrocarbon waste that contains 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl or 3-methyl-butyl, 1-ethyl-propyl, and 2-ethyl-propyl;
    a fluoroalkyl radical such as monofluoromethyl ($-CH_2F$), difluoromethyl ($-CHF_2$), trifluoromethyl ($-CF_3$), 1-fluoro-1-ethyl ($-CHFCH_3$), or 1,1-difluoro-1-ethyl ($-CF2CH3$);
    a cyclopropyl, cyclobutyl, or cyclopentyl radical;
    an aromatic heterocyclic group with 5 links, substituted or not, that contain 0.1, 2, 3, or 4 heteroatoms selected from among nitrogen, oxygen, and sulfur, with no more than one atom of sulfur or oxygen present in heterocycle A.
  The aromatic heterocycles are preferably: furan-2-yl, (O.CH:CH.CH:C—) or furan-3-yl, (CH:CH.O.CH:C—) or 1H-pyrrol-2-yl, (NH.CH:CH.CH:C—) or 1H-pyrrol-3-yl, (CH:CH.NH.CH:C—) or 1-methyl-pyrrol-2-yl, (N(CH3).CH:CH.CH:C—) or 1-methyl-pyrrol-3-yl, (CH:CH.N(CH3).CH:C—) or thiophen-2-yl, (S.CH:CH.CH:C—) or thiophen-3-yl, (CH:CH.S.CH:C—) or pyrazole-1-yl, (N:CH:CH.CH.N—) or 1H-pyrazole-3-yl, (CH:CH.NH.N:C—) or 1H-pyrazole-4-yl, (CH:N.NH.CH:C—) or 1-methyl-pyrazole-3-yl, (CH:CH.N(CH3).N:C—) or imidazol-1-yl (CH:N.CH:CH.N—) or 1H-imidazol-2-yl, (NH.CH:CH.N:C—) or 1H-imidazol-4-yl, (N:CH.NH.CH:C—) or oxazol-2-yl, (O.CH:CH.N:C—) or oxazol-4-yl, (N:CH.O.CH:C—) or oxazol-5-yl, (O.CH:N.CH:C—) or isoxazol-5-yl (O.N:CH.CH:C—) or isoxazol-4-yl, (CH:N.O.CH:C—) or isoxazol-3-yl, (CH:CH.O.N:C—) or thiazol-2-yl, (S.CH:CH.N:C—) or thiazol-4-yl, (N:CH.S.CH:C—) or thiazol-5-yl, (S.CH:N.CH:C—) or isothiazol-5-yl, (S.N:CH.CH:C—) or isothiazol-4-yl, (CH:N.S.CH:C—) or isothiazol-3-yl, (CH:CH.S.N:C—) or [1,2,4]triazol-1-yl, (CH:N.CH:N.N—) or 1H-[1,2,4]triazol-3-yl, (N:CH.NH.N:C—) or [1,2,4]oxadiazol-3-yl, (N:CH.O.N:C—) or [1,2,4]oxadiazol-5-yl, (O.N:CH.N:C—) or 5-methyl-[1,2,4]oxadiazol-3-yl, (N:C(CH3).O.N:C—) or 1H-tetrazol-5-yl, (NH.N:N.N:C—);
  an alkoxy ($R_1O-$) or alkylthio ($R_1S-$) group in which radical $R_1$ represents:
    a $C_1$-$C_5$ alkyl radical as previously defined,
    a monofluoromethyl or trifluoromethyl radical;
    a cyclopropyl, cyclobutyl, or cyclopentyl radical;
  a amino group of type II (II)

in which $R_2$ and $R_3$, identical or different, represent hydrogen, a $C_1$-$C_5$ alkyl radical as previously defined, a cyclopropyl group, or a trifluoromethyl group;
  a saturated cyclic amino group of type III (III)

in which n may be whole numbers 1 or 2;
  an alkoxycarbonyl group, preferably a methoxycarbonyl group (CH3OCO—), or an ethoxycarbonyl group ($CH_3CH_2OCO-$).

The invention also extends to additive salts from compounds of aforementioned formula I, with pharmaceutically acceptable mineral or organic acids.

More particularly, the present invention targets the use of compounds of formula I selected from among:

(3,4-Dichloro-phenyl)-(4-{[(6-pyrazole-1-yl-pyridine-2-ylmethyl)-amino]-methyl}-piperidine-1-yl)-methanone
(3-Chloro-4-fluoro-phenyl)-(4-{[(6-pyrazole-1-yl-pyridine-2-ylmethyl)-amino]-methyl}-piperidine-1-yl)-methanone
(4-Chloro-3-methyl-phenyl)-(4-{[(6-pyrazole-1-yl-pyridine-2-ylmethyl)-amino]-methyl}-piperidine-1-yl)-methanone
(3-Chloro-phenyl)-(4-{[(6-pyrazole-1-yl-pyridine-2-ylmethyl)-amino]-methyl}-piperidine-1-yl)-methanone
(4-{[(6-Pyrazole-1-yl-pyridine-2-ylmethyl)-amino]-methyl}-piperidine-1-yl)-m-tolyl-methanone
(3,4-Dichloro-phenyl)-{4-fluoro-4-{[(6-pyrazole-1-yl-pyridine-2-ylmethyl)-amino]-methyl}-piperidine-1-yl)-methanone
(3,4-Dichloro-phenyl)-(4-{[(6-imidazol-1-yl-pyridine-2-ylmethyl)amino]-methyl}-piperidine-1-yl)-methanone
(3,4-Dichloro-phenyl)-(4-{[(6[1,2,4,]triazol-1-yl-pyridine-2-ylmethyl)-amino]-methyl}-piperidine-1-yl)-methanone
(3,4-Dichloro-phenyl)-(4-{[(6-pyrrol-1-yl-pyridine-2-ylmethyl)-amino]-methyl}-piperidine-1-yl)-methanone
(3,4-Dichloro-phenyl)-(4-{[(6-methylamino-pyridine-2-ylmethyl)-amino]-methyl}-piperidine-1-yl)-methanone
(3,4-Dichloro-phenyl)-(4-fluoro-4-{[(6-methylamino-pyridine-2-ylmethyl)-amino]-methyl}-piperidine-1-yl)-methanone
(3,4-Dichloro-phenyl)-(4-{[(6-dimethylamino-pyridine-2-ylmethyl)-amino]-methyl}-piperidine-1-yl)-methanone
(3-Chloro-4-fluoro-phenyl)-(4-{[(6-dimethylamino-pyridine-2-ylmethyl)-amino]-methyl}-4-fluoro-piperidine-1-yl)-methanone
(3,4-Dichloro-phenyl)-{4-{[(6-dimethylamino-pyridine-2-ylmethyl)-amino]-methyl}-4-fluoro-piperidine-1-yl)-methanone
(3,4-Dichloro-phenyl)-[4-({[6-(ethyl-methyl-amino)-pyridine-2-ylmethyl]-amino}-methyl)-4-fluoro-piperidine-1-yl]-methanone
(3,4-Dichloro-phenyl)-[4-({[6-(methyl-propyl-amino)-pyridine-2-ylmethyl]-amino}-methyl)-piperidine-1-yl]-methanone
(4-{[(6-Azetidin-1-yl-pyridine-2-ylmethyl)-amino]-methyl}-piperidine-1-yl)-(3,4-dichloro-phenyl)-methanone
(4-{[(6-Azetidin-1-yl-pyridine-2-ylmethyl)-amino]-methyl}-4-fluoro-piperidine-1-yl)-(3,4-dichloro-phenyl)-methanone
(4-{[(6-Cyclopentyl-pyridine-2-ylmethyl)-amino]-methyl}-piperidine-1-yl}-(3,4-dichloro-phenyl)-methanone
(4-{[(6-Chloro-pyridine-2-ylmethyl)-amino]-methyl}-piperidine-1-yl)-(3,4-dichloro-phenyl)-methanone
(3,4-Dichloro-phenyl)-[4-({[6-(1H-pyrazole-3-yl)-pyridine-2-ylmethyl]-amino}-methyl)-piperidine-1-yl]-methanone
(3,4-Dichloro-phenyl)-[4-fluoro-4-{{[6-(1H-pyrazole-3-yl)-pyridine-2-ylmethyl]-amino}-methyl)-piperidine-1-yl]-methanone
(3,4-Dichloro-phenyl)-[4-fluoro-4-({[6-(1-methyl-pyrazole-3-yl)-pyridine-2-ylmethyl]-amino}-methyl)-piperidine-1-yl]-methanone
(3,4-Dichloro-phenyl)-[4-({[6-(1H-imidazol-2-yl)-pyridine-2-ylmethyl]-amino}-methyl)-piperidine-1-yl]-methanone
(3,4-Dichloro-phenyl)-(4-{[(6-thiazol-2-yl-pyridine-2-ylmethyl)-amino]-methyl}-piperidine-1-yl)-methanone
(3,4-Dichloro-phenyl)-(4-fluoro-4-{[(6-thiazol-2-yl-pyridine-2-ylmethyl)-amino]-methyl}-piperidine-1-yl)-methanone
(3,4-Dichloro-phenyl)-[4-({[6-(1H-pyrrol-2-yl)-pyridine-2-ylmethyl]-amino}-methyl)-piperidine-1-yl]-methanone
(3,4-Dichloro-phenyl)-(4-{[(6-thiophen-2-yl-pyridine-2-ylmethyl)amino]-methyl}-piperidine-1-yl)-methanone
(3,4-Dichloro-phenyl)-(4-fluoro-4-{[(6-thiophen-2-yl-pyridine-2-ylmethyl)-amino]-methyl}-piperidine-1-yl)-methanone
(3,4-Dichloro-phenyl)-(4-{[(6-furan-2-yl-pyridine-2-ylmethyl)-amino]-methyl}-piperidine-1-yl)-methanone
(3,4-Dichloro-phenyl)-(4-fluoro-4-{[(6-furan-2-yl-pyridine-2-ylmethyl)-amino]-methyl}-piperidine-1-yl)-methanone
(3-Chloro-4-fluoro-phenyl)-(4-fluoro-4-{[(6-furan-2-yl-pyridine-2-ylmethyl)-amino]-methyl}-piperidine-1-yl)-methanone
(3,4-Dichloro-phenyl)-(4-{[(6-oxazol-5-yl-pyridine-2-ylmethyl)-amino]-methyl}-piperidine-1-yl)-methanone
(3,4-Dichloro-phenyl)-(4-fluoro-4-{[(6-oxazol-5-yl-pyridine-2-ylmethyl)-amino]-methyl}-piperidine-1-yl)-methanone
(3,4-Dichloro-phenyl)-(4-fluoro-4-{[(6-furan-3-yl-pyridine-2-ylmethyl)-amino]-methyl}-piperidine-1-yl)-methanone
(3,4-Dichloro-phenyl)-[4-({[6-(5-methyl[1,2,4]oxadiazol-3-yl)-pyridine-2-ylmethyl]-amino}-methyl)-piperidine-1-yl]-methanone
(3,4-Dichloro-phenyl)-(4-{[(6-methyl-pyridine-2-ylmethyl)-amino]-methyl}-piperidine-1-yl)-methanone
(3,4-Dichloro-phenyl)-(4-{[(6-isopropyl-pyridine-2-ylmethyl)-amino]-methyl}-piperidine-1-yl)-methanone
(3,4-Dichloro-phenyl)-(4-{[(6-cyclopropyl-pyridine-2-ylmethyl)-amino]-methyl}-4-fluoro-piperidine-1-yl)-methanone
(3,4-Dichloro-phenyl)-(4-fluoro-4-{[(6-fluoromethyl-pyridine-2-ylmethyl)-amino]-methyl}-piperidine-1-yl)-methanone
(3,4-Dichloro-phenyl)-(4-{[(6-difluoromethyl-pyridine-2-ylmethyl)-amino]-methyl}-piperidine-1-yl)-methanone
(3,4-Dichloro-phenyl)-(4-{[(6-difluoromethyl-pyridine-2-ylmethyl)-amino]-methyl}-4-fluoro-piperidine-1-yl)-methanone
(3,4-Dichloro-phenyl)-[4-fluoro-4-({[6-(1-fluoro-ethyl)-pyridine-2-ylmethyl]-amino}-methyl)-piperidine-1-yl]-methanone
6-({[1-(3,4-Dichloro-benzoyl)-piperidine-4-ylmethyl]-amino}-methyl)-pyridine-2-carboxylicacidmethylester
6-({[1-(3,4-Dichloro-benzoyl)-piperidine-4-ylmethyl]-amino}-methyl)-pyridine-2-carboxylicacidethylester
(3,4-Dichloro-phenyl)-(4-{[(6-methoxy-pyridine-2-ylmethyl)-amino]-methyl}-piperidine-1-yl)-methanone
(3,4-Dichloro-phenyl)-(4-fluoro-4-{[(6-methoxy-pyridine-2-ylmethyl)-amino]-methyl}-piperidine-1-yl)-methanone
(3,4-Dichloro-phenyl)-(4-fluoro-4-{[(6-isopropyloxy-pyridine-2-ylmethyl)-amino]-methyl}-piperidine-1-yl)-methanone
(4-{[(6-Cyclopentyloxy-pyridine-2-ylmethyl)-amino]-methyl}-piperidine-1-yl)-(3,4-dichloro-phenyl)-methanone
(3,4-Dichloro-phenyl)-{4-{[(6-methylsulfanyl-pyridine-2-ylmethyl)-amino]-methyl}-piperidine-1-yl)-methanone
(3,4-Dichloro-phenyl)-(4-{[(6-fluoro-pyridine-2-ylmethyl)-amino]methyl}-piperidine-1-yl)-methanone
(3,4-Dichloro-phenyl)-(4-fluoro-4-{[(6-fluoro-pyridine-2-ylmethyl)-amino]-methyl}-piperidine-1-yl)-methanone
(3,4-Dichloro-phenyl)-(4-fluoro-{[(3-fluoro-pyridine-2-ylmethyl)-amino]-methyl}-piperidine-1-yl)-methanone (4-{[(4-Chloro-pyridine-2-ylmethyl)-amino]-methyl}-piperidine-1-yl)-(3,4-dichloro-phenyl)-methanone (3-Chloro-4-fluoro-phenyl)-(4-fluoro-4-{[(5-methyl-6-furan-2-yl-pyridine-2-ylmethyl)-amino]-methyl}-piperidine-1-yl)-methanone (3-Chloro-4-fluoro-phenyl)-[4-fluoro-4-({[5-methyl-6-(1H-pyrazole-3-yl)-2-yl-pyridine-2-ylmethyl]-amino}-methyl)-piperidine-1-yl]-methanone (3-Chloro-4-fluoro-phenyl)-(4-fluoro-4-{[(5-methyl-6-methylamino-pyridine-2-ylmethyl)-amino]-methyl}-piperidine-1-yl)-methanone (4-{[(6-Azetidin-1-yl-pyridine-2-ylmethyl)-amino]-methyl}-4-fluoro-piperidine-1-yl)-(3-chloro-4-fluoro-phenyl)-methanone (3-Chloro-4-fluoro-phenyl)-(4-fluoro-4-{[(6-oxazol-5-yl-pyridine-2-ylmethyl)-amino]-methyl}-piperidine-1-yl)-methanone (3-Chloro-4-fluoro-phenyl)-(4-fluoro-4-{[(6-ethylamino-pyridine-2-ylmethyl)-amino]-methyl}-piperidine-1-yl)-methanone (3-Chloro-4-fluoro-phenyl)-(4-fluoro-4-{[(6-methylamino-pyridine-2-ylmethyl)-amino]-methyl}-piperidine-1-yl)-methanone (3-Chloro-4-methyl-phenyl)-(4-fluoro-4-{[(6-dimethylamino-pyridine-2-ylmethyl)-amino]-methyl}-piperidine-1-yl)-methanone (3-Chloro-4-fluoro-phenyl)-{4-fluoro-4-{[(5-methyl-6-dimethylamino-pyridine-2-ylmethyl)-amino]-methyl}-piperidine-1-yl)-methanone (3-Chloro-4-fluoro-phenyl)-[4-fluoro-4-({[6-(1H-pyrazole-3-yl)-pyridine-2-ylmethyl]-amino}-methyl)-piperidine-1-yl]-methanone (3,4-Dichloro-phenyl)-(4-fluoro-4-{[(3-methyl-6-dimethylamino-pyridine-2-ylmethyl)-amino]-methyl}-piperidine-1-yl)-methanone (3-Chloro-4-fluoro-phenyl)-(4-fluoro-4-{[(6-pyrazole-1-yl-pyridine-2-ylmethyl)-amino]-methyl}-piperidine-1-yl)-methanone (3,4-Dichloro-phenyl)-(4-fluoro-4-{[(5-methyl-pyridine-2-ylmethyl)-amino]-methyl}-piperidine-1-yl)-methanone (3-Chloro-4-fluoro-phenyl)-(4-fluoro-4-{[(5-methyl-pyridine-2-ylmethyl)-amino]-methyl}-piperidine-1-yl)-methanone (3-Chloro-4-fluoro-phenyl)-(4-fluoro-4-{[(6-diethylamino-pyridine-2-ylmethyl)-amino]-methyl}-piperidine-1-yl)-methanone (3-Chloro-4-fluoro-methyl)-(4-fluoro-4-{[(5-methyl-6-chloro-pyridine-2-ylmethyl)-amino]-methyl}-piperidine-1-yl)-methanone (3-Chloro-4-fluoro-phenyl)-(4-fluoro-4-{[(4-methyl-6-dimethylamino-pyridine-2-ylmethyl)-amino]-methyl}-piperidine-1-yl)-methanone (3-Chloro-4-fluoro-phenyl)-(4-fluoro-4-{[(5-methyl-6-pyrazole-1-yl-pyridine-2-ylmethyl)-amino]-methyl}-piperidine-1-yl)-methanone (3-Chloro-phenyl)-(4-fluoro-4-{[(6-dimethylamino-pyridine-2-ylmethyl)-amino]-methyl}-piperidine-1-yl)-methanone Within the context of the present invention, the preferred compounds of formula (I) are:

(3-Chloro-4-fluorophenyl)-[4-fluoro-{[(5-methyl-pyridine-2-ylmethyl)-amino]-methyl}-piperidine-1-yl)-methanone, with A=H, u=CH$_3$, v and w=H, X=F, y=Cl, and z=F, and (3-Chloro-4-fluorophenyl)-(4-fluoro-{[(5-methyl-6-methylamino-pyridine-2-ylmethyl)-amino]-methyl}-piperidine-1-yl)-methanone, with A=NHCH$_3$, u=CH3, v and w=H, X=F, y=Cl, and z=F as well as their additive salts with pharmaceutically acceptable mineral or organic acids. These compounds are referred to hereafter as (Ia) and (Ib).

The preparation of compounds (Ia) and (Ib) as well as their analytical characteristics are reported in patent WO 02/064585.

The invention also extends to pharmaceutical compounds that contain as an active ingredient at least one of the derivatives of general formula (I) or one of its salts or hydrates thereof in combination with one or more inert media or other pharmaceutically acceptable vehicles.

Pharmaceutical compounds according to the invention may be, for example, compounds that can be administered by the oral, nasal, sublingual, rectal, transcutaneous, and parenteral routes. As examples of compounds that may be administered by the oral route, the most common include tablets, gelatin capsules, granules, powders, and oral solutions and suspensions. Pharmaceutical examples of compounds that contain products of formula (I) are reported in patent WO 98/22459.

The effective dose of a compound of the invention varies as a function of a number of parameters such as, for example: the administration route chosen; the subject's weight, age, and sex; the state of advancement of the pathology under treatment; and the sensitivity of the treated individual. As a consequence, the optimal dosage must be determined as a function of the parameters deemed relevant by the specialist in the art.

As illustrative examples of chronic neuropathic and psychogenic pain that is potentially sensitive to the action of compounds of general formula (I), the following may be cited more specifically: peripheral or central neuropathic pain that results from nerve lesions of traumatic origin (a cerebral vascular accident, for example), of metabolic origin (diabetes, for example), infectious origin (HIV, shingles, and herpes, for example), toxic origin (arsenic and lead, for example), invasive origin (cancer pain), or congenital origin; pain from phantom limbs; cephalgias; noninflammatory articular pain (osteoarthritis, for example); fibromyalgia; rachidian pain; postoperative pain; and from other causes of neuropathic pain such as multiple sclerosis and chronic pain. Pain is considered to be chronic when the patient reports suffering for a period that exceeds six months. Among chronic pain, in addition to pain associated with fibromyalgia, it would be appropriate to cite as illustrative and non-limiting examples pain arising from fibrous tissues, muscles, tendons, ligaments and other sites, abdominal pain, diarrhea (notably in the case of irritable bowel syndrome), and chronic back pain.

In particular, the present invention targets the treatment of fibromyalgia syndrome. Fibromyalgia is a chronic syndrome characterized by a morning sensation of pain or burning and stiffness, primarily involving fibrous, articular, and periarticular tissue, and by a feeling of profound fatigue. It is appropriate here to recall that fibromyalgia presents a set of symptoms which include nonrestorative sleep, headaches, digestive disorders, depressed state, muscle spasms, face pain, and numbness.

The invention also targets the treatment of certain symptoms of chronic fatigue syndrome, which is characterized by a state of exhaustion or fatigue that most notably results in muscle spasms and/or pain.

Study of the Pharmacological Properties of Compounds of Formula (I)

Measuring the analgesic activity of products (Ia) and (Ib) makes it possible to demonstrate:
the effectiveness of compounds of formula (I) in representative animal models of neuropathic pain; and
their unique analgesic activity profile.

Thus are illustrated the improvements in analgesic techniques and treatments which are the subject of the present invention.

As examples, we describe the analgesic activities of products (Ia) and (Ib) obtained in tests of peripheral and central neuropathy. These examples in no way limit the scope of the invention.

An Illustration of the Curative Aspect of the Analgesic Effect Produced by Compounds of Formula (I)

Case 1: Treatment with Compound (Ia) Once Chronic Pain is Established

The central neuropathy test used is conducted in the rat according to a method analogous to that described by Hao and Xu in Pain 1996, 66, 279-286. The product to be tested is delivered at a constant rate by means of an osmotic pump (Alzet, model 2ML2) for 14 days. The pumps are implanted 28 days after spinal cord lesion and then explanted at the treatment's end. In this model, it was established that at 28 days post-lesion the animal is in a phase of chronic hypersensitivity which then lasts for several months. In this experiment, the hypersensitivity of the lesioned animals treated with compound (Ia) or with saline solution was measured. The pain threshold was objectified by the animal's persistent vocalization in response to a stimulation of increasing intensity in the sensitive region by means of von Frey hairs. Thus, analgesia is all the more effective as the vocalization amplitude threshold is raised. The fumarate of compound (Ia) is administered at 0.63 mg/rat/day. The pumps implanted in the group of lesioned control animals release a 0.9% NaCl solution (saline)/rat/day.

The stimulation sensitivity tests by means of von Frey hairs are conducted 3 days after implantation of the osmotic pump and continue regularly for 28 days. The doses refer to the weight of non-salified compound.

Figure 3:
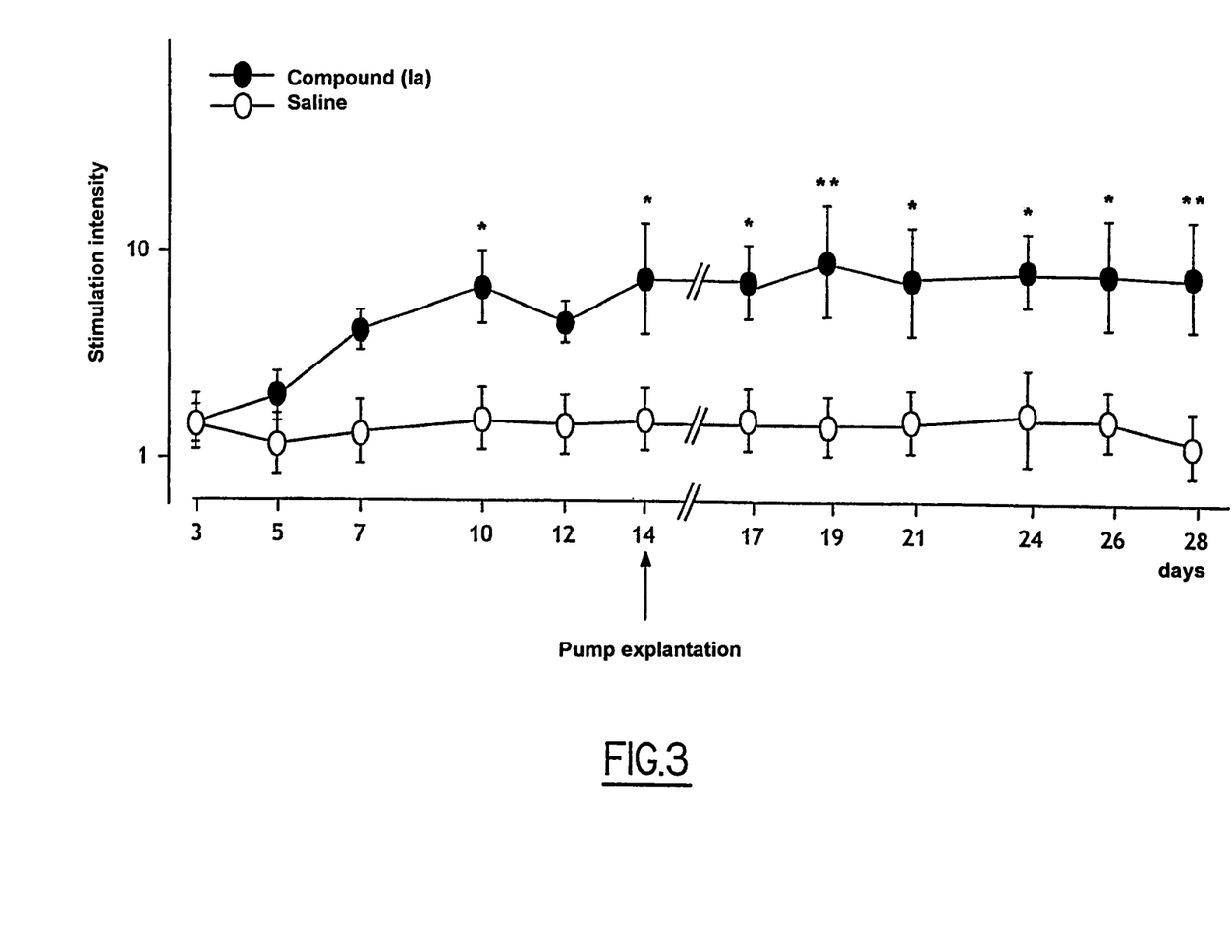
FIG. 3 shows a comparison between compound (Ia) and saline and their effects on stimulation sensitivity as discussed in the examples.

The effects obtained with compound (Ia) in comparison with those of the lesioned control animals that received saline solution are represented in FIG. 3 in the appendix. In this model, antidepressant and anti-inflammatory agents, as well as morphine compounds, are inactive.

Results

In the lesioned animals treated with saline solution the stimulation that initiates vocalization is of very low intensity and remains so throughout the experiment (i.e., 28 days post-lesion). Thus, the lesioned animals have developed chronic hypersensitivity. The animals treated by means of compound (Ia) tolerated stimulation of higher intensity that did the control animals and this was the case at all measurement points throughout the treatment. This state, similar to analgesia, is statistically significant as of the tenth day of treatment. Thus, compound Ia possesses symptomatic analgesic activity. After treatment is interrupted (i.e., after day 15 in FIG. 3 in the appendix), analgesia persists and is maintained at the same level as that attained at the treatment's end, in fact significantly at all measurement times throughout the remainder of the experiment (i.e., 14 days following pump explantation).

Thus, compound (Ia) also possesses a curative analgesic activity.

The results of the experiment show that treatments using compounds of formula (I) produce:
a phase of symptomatic analgesia;
a phase of curative analgesia.

Case 2: Treatment with Compounds (Ia) and (Ib) when Pain has Yet to Develop

The peripheral neuropathy test used was conducted in the rat according to a method analogous to that described by Vos in J. Neurosci. 1994, 14, 2708-2723. The product to be tested is delivered at a constant rate (0.12 ml/day) by means of an osmotic pump (Alzet, model 2ML2) for 14 days. The pumps are implanted 24 hours before lesion (unilateral ligature of the infraorbital nerve) and then explanted at the treatment's end. The pumps are implanted subcutaneously via a transverse incision made in the dorsal skin of the rat. Evaluation of the intensity of perceived pain is objectified from a series of behavioral signs observed in response to mechanical stimulation of the region lesioned by means of von Frey hairs. Stimulations are applied in order of increasing intensity. Intensity of perceived pain is evaluated from the following criteria: 0, no response by the animal; 1, detection (i.e., the rat turns its head towards the object used for stimulation); 2, withdrawal (i.e., the rat turns away or makes a withdrawal movement with its head to avoid the object used for stimulation); 3, flight or attack (i.e., the rat avoids the object by moving its body or deliberately attacks the object used for stimulation); 4, face rubbing (i.e., the rat rubs the area of stimulation three times in succession). The response level by the non-lesioned animals was 0 or 1.

The fumarate of compound (Ia) is administered at 0.63 mg/rat/day; the glycolate of compound (Ib) at 0.16 mg/rat/day; morphine hydrochloride at 5 mg/rat/day, and baclofen at 1.06 mg/rat/day. All the compounds are administered in solution in distilled water. The pumps implanted in the control animals release a 0.9% NaCl solution (saline)/rat/day; the doses refer to the weight of non-salified compound.

Figure 7:
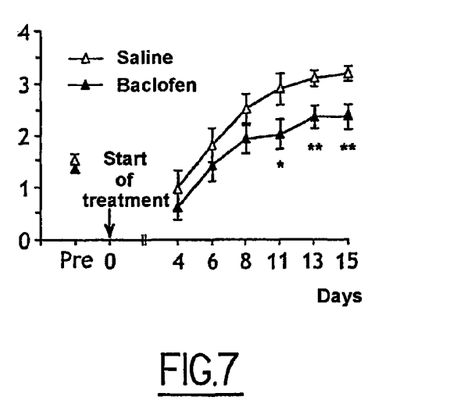
FIG. 7 shows a comparison between baclofen and saline for reducing an animal's hypersensitivity to stimulation as discussed in the examples.
Figure 8:
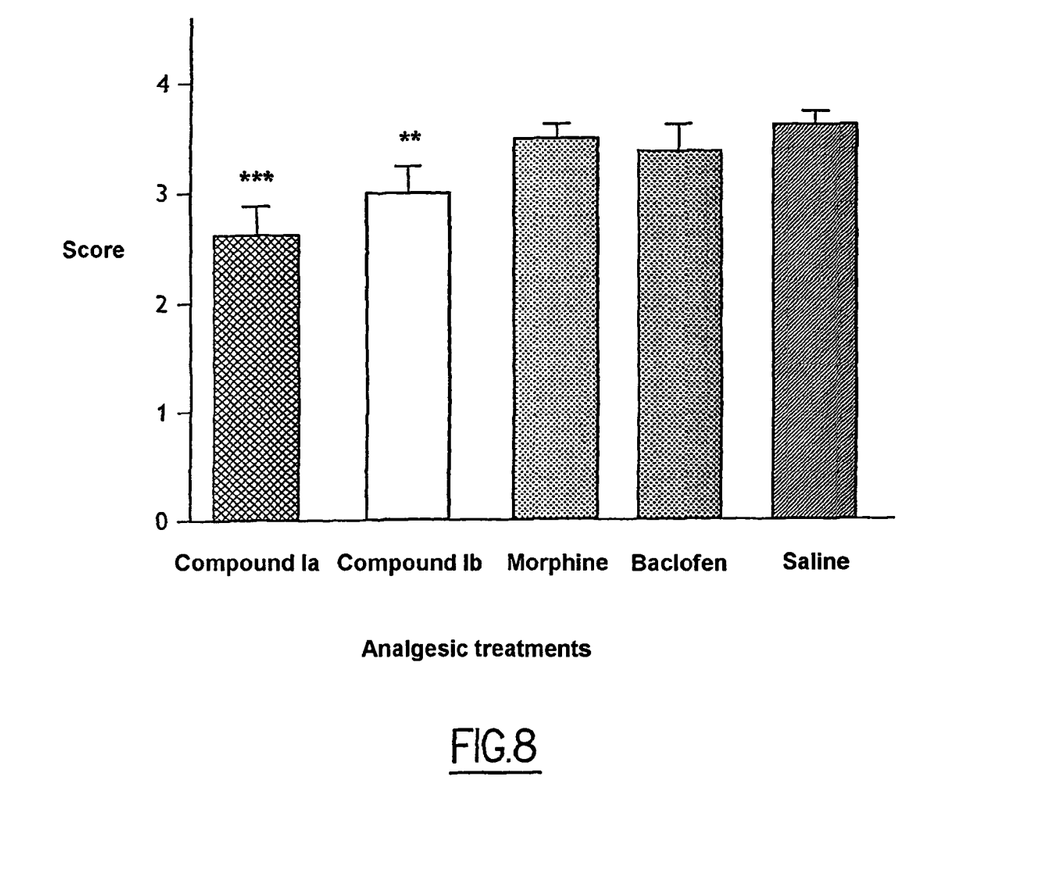
FIG. 8 shows a comparison of the analysis effects of compounds (Ia) and (Ib), morphine, baclofen, and saline, six days after treatment.

The effects obtained with compounds (Ia), (Ib), and the products chosen as references are represented in FIGS. 4 to 8 in the appendix. FIGS. 4 to 7 represent the analgesic effects of the various products evaluated at days 4, 6, 8, 11, and 13 of treatment and 1 day following explantation of the pump (day 15). FIG. 8 represents the analgesic effects of the various products measured at day 21, which is 6 days following the treatment's end. In this model, it has been established previously that antidepressant agents are inactive whereas baclofen is the agent with the highest activity.

The individual scores of each animal represent the average (±standard error) obtained after application of the von Frey hairs. The comparison of the results between the various groups as well as the progress of the values obtained over time are performed using an analysis of variance test (ANOVA), followed by a Dunnett's multiple comparison test.

Results

The analgesic effects observed vary differently over the course of the time as a function of the products evaluated. The resolution of the evaluation system adopted (evaluation criteria from 0 to 4) has as a consequence small relative variation between the amplitudes of the analgesic effects observed.

Figure 4:
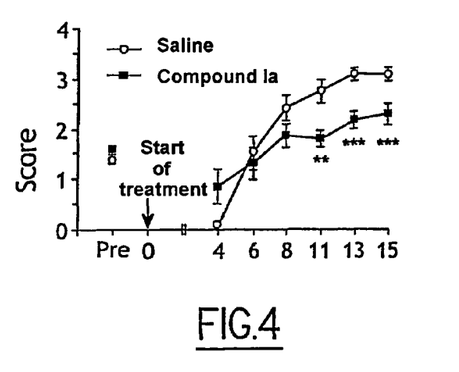
FIG. 4 shows a comparison between compound (Ia) and saline for reducing an animal's hypersensitivity to stimulation as discussed in the examples.
Figure 5:
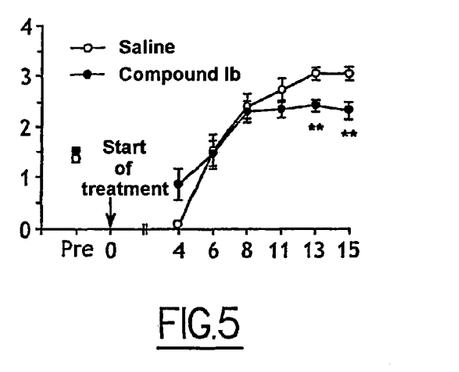
FIG. 5 shows a comparison between compound (Ib) and saline for reducing an animal's hypersensitivity to stimulation as discussed in the examples.
Figure 6:
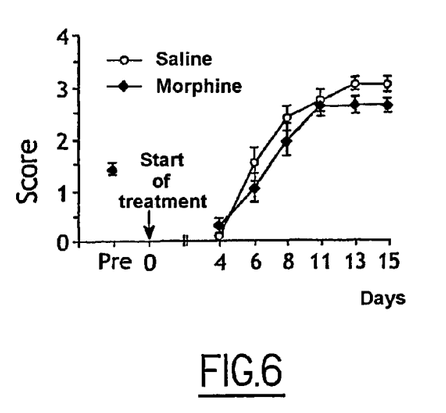
FIG. 6 shows a comparison between morphone and saline for reducing an animal's hypersensitivity to stimulation as discussed in the examples.

The comparison between product (Ia) and saline shows that compound (Ia) reduced the animal's hypersensitivity (allodynia) to stimulation (comparable to an analgesic effect), and did so significantly after day 11 (FIG. 4). Compound (Ib) reduced hypersensitivity significantly only after day 13 (FIG. 5). Morphine was inactive under the experimental conditions (FIG. 6) whereas baclofen also had a significant analgesic effect after day 11 (FIG. 7).

Six days after the treatment's end, the animals treated with compounds (Ia) and (Ib) continued to show a significant analgesic effect, whereas the effect of morphine and of baclofen disappeared completely (FIG. 8). Moreover, the amplitude of the analgesia produced by compounds (Ia) and

(Ib) measured 6 days after the treatment's end is not statistically different from the amplitude measured at the treatment's end (i.e., day 15).

The results of the experiment show that a treatment by means of compounds (Ia) and (Ib):
- decreases perceived pain intensity after a nerve lesion of peripheral origin and does so with an amplitude at least equivalent to that of the reference product recognized as the most effective in this neuropathic pain model (i.e., baclofen);
- produces an analgesic effect that persists and remains stable for at least 6 days following the treatment's end which is contrary to that observed with baclofen.

It arises from the studies that certain compounds of formula (I), as well as their additive salts with pharmaceutically acceptable mineral or organic acids, are effective in the treatment of chronic neuropathic pain of peripheral and central origin. The analgesia that they provide, moreover, has a single and completely remarkable development profile. Thus, the analgesia persists and is maintained at a stable level far beyond the treatment period and does so regardless of the treatment plan (pre- or post-lesion). This specific analgesia phase, referred to as "curative" in the present invention, is, contrary to the symptomatic phase, specific to compounds of formula (I). Such an analgesic development profile has never before been demonstrated, not only with 5-HT$1_A$ agonists but also with other agents that possess analgesic properties. For this reason, compounds of formula (I) clearly make possible improvements in current analgesia treatment.

The invention claimed is:

1. A method of reducing chronic pain symptoms in a subject in need thereof comprising administering to the subject an effective dose of a compound of formula (I), (I)

wherein
- u represents a methyl radical;
- v represents a hydrogen atom;
- w represents a hydrogen atom;
- x represents a fluorine atom;
- y represents a chlorine atom;
- z represents an atom of fluorine or chlorine;

A is selected from the group consisting of:
- an atom of hydrogen, fluorine, or chlorine;
- an amino group of type II (II)

in which $R_2$ and $R_3$, identical or different, represent hydrogen, $C_1$-$C_5$ alkyl radical, wherein said C1-C5 alkyl radical is a straight or branched saturated aliphatic hydrocarbon moiety that contains 1 to 5 carbon atoms, a cyclopropyl group, or a trifluoromethyl group, and wherein said compound is selected from the group consisting of (3-Chloro-4-fluorophenyl)-[4-fluoro-{[(5-methyl-pyridine-2-ylmethyl)-amino]-methyl}-piperidine-1-yl)-methanone, wherein A=H, u=CH$_3$, v and w=H, X=F, y=Cl, and z=F (compound Ia), (3-Chloro-4-fluorophenyl)-(4-fluoro-{[(5-methyl-6-methylamino-pyridine-2-ylmethyl)-amino]-methyl}-piperidine-1-yl)-methanone, wherein A=NHCH$_3$, u=CH$_3$, v and w=H, X=F, y=Cl, and z=F (compound Ib) and pharmaceutically acceptable salts thereof, and wherein the dose is administered prior to the onset of the chronic pain symptoms in the subject and wherein the reduction of chronic pain symptoms is associated with analgesia which is produced in the subject by the compound and which may persist and attenuate later pain development after the compound is no longer present in the body of the subject.

2. The method according to claim 1, wherein said pain is postoperative pain or pain associated with nervous system attack.

3. The method of claim 2 where said pain associated with nervous system attack is phantom pain or pain associated with rachidian lesions.

4. The method of claim 1, wherein said pharmaceutically acceptable salts comprise pharmaceutically acceptable mineral or organic acids.

5. The method of claim 1, wherein said compound or pharmaceutically acceptable salts thereof are administered in pharmaceutical compounds.

6. The method of claim 5, wherein said pharmaceutical compounds are administered by an oral, nasal, sublingual, rectal, transcutaneous or parenteral route.

7. The method of claim 6, wherein said pharmaceutical compounds administered by an oral route are selected from the group consisting of tablets, gelatin capsules, granules, powders, solutions or suspensions.

* * * * *